United States Patent [19]

Kankare

[11] Patent Number: 4,561,962
[45] Date of Patent: Dec. 31, 1985

[54] ION-SELECTIVE ELECTRODE AND PROCEDURE FOR MANUFACTURING SAME

[75] Inventor: Jouko Kankare, Turku, Finland

[73] Assignee: Fluilogic Systems Oy, Finland

[21] Appl. No.: 674,720

[22] Filed: Dec. 14, 1984

Related U.S. Application Data

[63] Continuation of Ser. No. 482,549, Apr. 6, 1983, abandoned.

[51] Int. Cl.⁴ ............................................. G01N 27/30
[52] U.S. Cl. ..................................... 204/415; 204/418
[58] Field of Search ............... 204/415, 416, 418, 1 P, 204/1 A; 128/635

[56] References Cited

U.S. PATENT DOCUMENTS

| | | | |
|---|---|---|---|
| 3,598,713 | 8/1971 | Baum et al. | 204/418 X |
| 3,691,047 | 9/1972 | Ross et al. | 204/418 |
| 3,835,011 | 9/1974 | Baum et al. | 204/418 |
| 3,932,233 | 1/1976 | Ruzicka et al. | 204/418 |
| 4,115,209 | 9/1978 | Frieser et al. | 204/418 X |
| 4,242,191 | 12/1980 | Schindler et al. | 204/418 |
| 4,251,470 | 2/1981 | Owen et al. | 204/418 X |
| 4,271,002 | 6/1981 | Hawkins | 204/418 |
| 4,379,041 | 4/1983 | Petranek et al. | 204/418 |

Primary Examiner—Andrew H. Metz
Assistant Examiner—Nam X. Nguyen
Attorney, Agent, or Firm—Pahl, Lorusso & Loud

[57] ABSTRACT

The invention concerns an ion-selective electrode comprising a polymer membrane, and its manufacturing procedure. Selectivity of the electrode to a given ion has been achieved in that the membrane is of material polymerized from a substance or mixture of substances containing the ion in question and from which after the polymerizing step a quantity of ions of this kind has been removed so that gaps of equivalent size have been produced in the material. An example of said polymerizable substances is a mixture formed by allyloxy-substituted propyleneglycol phosphate and calciumbisdiallyl phosphate, which is used in making a calcium-selective electrode. If in the example mixture calcium is replaced by another ion, an electrode which is sensitive to this particular ion is similarly obtained. It is to advantage in view of the electrode's mechanical properties to make the electrode without internal solution by affixing the polymer membrane directly on the surface of a semiconductor body consisting e.g. of stannic dioxide.

2 Claims, 1 Drawing Figure

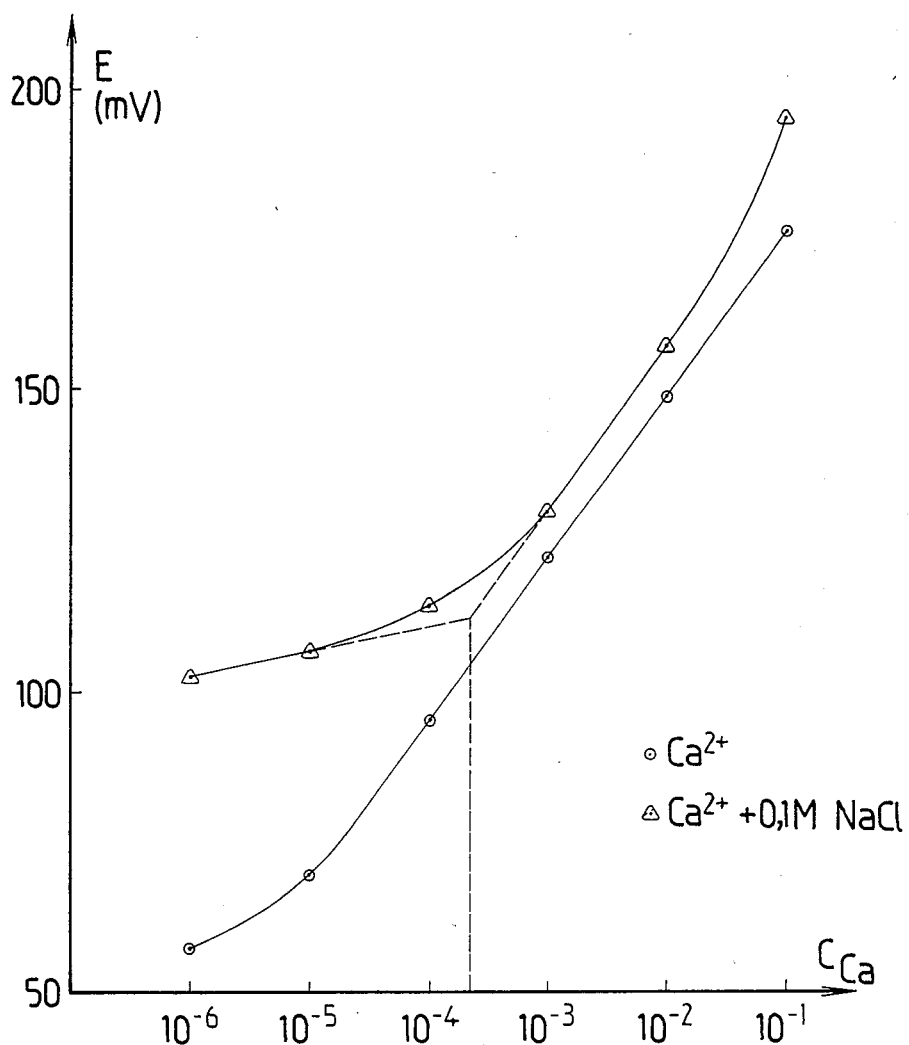

ION-SELECTIVE ELECTRODE AND PROCEDURE FOR MANUFACTURING SAME

This application is a continuation of U.S. patent application Ser. No. 482,549, filed Apr. 6, 1983, now abandoned.

The present invention concerns an ion-selective electrode comprising a conductor or semiconductor body and a membrane of polymer material which in the measurement carried out with the electrode separates said conductor or semiconductor body from the solution under measurement.

The ion-selective electrode is an instrument for analysis that is used for determination of a given ion's concentration in a solution. The determination is based on the fact that within certain limits the potential of the electrode is directly proportional to the logarithm of the ion's activity. The most essential property of an ion-selective electrode is its selectivity, that is, the feature that the results that are obtained are maximally independent of other ions which are present.

Such ion-selective electrodes are known in the art which comprise a liquid membrane consisting of an organic liquid scantily soluble in water and, dissolved therein, a compound, this compound forming with the ion to be determined either a complex or an ion pair and hereby increasing the ion's distribution coefficient between the organic phase and the aqueous phase. However, these electrodes are encumbered by the drawback that the gradual dissolving of the sensor and/or the organic solvent in the water phase puts a limit to the service life of the electrode, and moreover it is necessary to find for each ion a suitable organic compound, and this has to take place by experimentation, in lack of an exact theory.

In prior art is further known an ion-selective electrode where the membrane has been formed with polymer material replacing the organic liquid, this polymer material containing active functional groups. A calcium-selective electrode for instance is constructed by branching triallyl phosphate to a polystyrene/butadiene trunk and thereafter partially hydrolysing the phosphate ester groups into acid form. Such electrodes are mechanically durable and no dissolving reducing the life span of the electrode takes place in them, but the selectivity for instance of the calcium electrode mentioned with regard to sodium is inadequate with a view to clinical uses.

The object of the invention is to form an ion-selective electrode comprising a membrane of polymer material, in which the drawbacks mentioned above have been avoided and which has better selectivity than before. The electrode of the invention is characterized in that the membrane consists of polymer material produced from a polymerizable substance, or mixture of substances, containing the ion desired to be determined, and from which after the polymerizing step ions of the kind mentioned have been removed thereby producing in the material gaps corresponding to the ions that have departed.

It is believed that the method for producing the membrane belonging to the electrode of the invention could be termed "template polymerizing", in which is used as "template" the ion that is removed from the membrane in the final step e.g. by extraction. The gaps left in the membrane, corresponding to the removed ions, are such that those ions which are meant to be determined in the measurement made with the electrode fit into them like a key fits into the lock. The invention affords the particular advantage that it becomes possible to manufacture electrodes sensitive to different kinds of ions merely by changing, in connection with the manufacturing of the membrane, the template ion contained in the mixture that is being polymerized.

The membrane which is part of the ion-selective electrode of the invention is preferably cross-linked polymer material which has been made by polymerizing a mixture consisting of a bifunctional, polymerizable compound and of a salt reacting with it and containing the ion to be determined. When manufacturing a membrane of this kind, it is an easy thing to control the degree of cross-linking by means of the duration of the polymerizing reaction.

It is possible to construct the electrode of the invention so that the polymer membrane is located between the solution which is the object of measurement and the internal reference solution of the electrode. However, a design more favourable in view of the electrode's mechanical properties is that in which the membrane has been applied on the surface of a conductor or semiconductor body as a material layer covering the body, whereby no internal reference solution whatsoever is needed. This type of electrode without internal solution is well usable e.g. with automatic analysers. To be sure, electrodes without internal solution have presented the drawback that the boundary surface between the metallic conductor body and the membrane is indefinite, with consequent instability, but this can be reduced by replacing the metal with an n-type oxidic semiconductor, stannic oxide. Moreover, the stability of the electrode without internal solution can be improved by providing, by means of copolymerizing, reduction/oxidation centres within the membrane. Such centres may be obtained, e.g. by adding, in connection with the membrane-forming process, vinyl ferrosene to the mixture that is being polymerized.

A further object of the invention is a procedure for manufacturing the ion-selective electrode above described. As taught by this procedure, a membrane of polymer material is formed, this membrane being connected to a conductor or semiconductor body so that in the measurement performed with this electrode the membrane will separate the conductor or semiconductor body from the solution which is the measuring object. The procedure is characterized in that the membrane is formed of polymer material which is manufactured from a polymerizable substance or mixture of substances containing the ion which one desires to determine, and from which after the polymerizing step ions of the kind mentioned are removed so that gaps equivalent to the departing ions are produced within the material.

One favourable embodiment of the procedure of the invention is characterized in that the polymer material is prepared by polymerizing a mixture composed of a polyfunctional, polymerizing compound and of a salt reacting therewith which contains the ion that is to be determined. This polymerizing may be effected with the aid of heat, and the degree of cross-linking of the polymer may then be controlled by regulating the duration of its heating.

Another favourable embodiment of the procedure of the invention is characterized in that the polymerizable substance or mixture of substances is spread over the surface of a conductor or semiconductor body, where it is polymerized to become a polymer layer covering the body and forming a membrane. In this manner is obtained a mechanically firm electrode without internal solution, suitable for use in connection with automatic analyzers.

In order to illustrate the invention, there shall now be described as example the manufacturing of a calcium-selective electrode according to the invention, as well as measurements carried out with this electrode. In connection with the description, reference is made to the attached drawing, showing graphically the potential of the electrode plotted over the calcium concentration.

A BRIEF DESCRIPTION OF DRAWING

The sole FIGURE of the drawing is a graph of cell potentials in mV, for an electrode according to the present invention, plotted over the logarithm of calcium ion concentration in water and in 0.1M NaCl.

MANUFACTURING THE INITIAL SUBSTANCES FOR THE MEMBRANE POLYMERISATION

Allyloxy-substituted propyleneglycol telomer

A solution containing 50 g allylglycidyl ether (Aldrich, 99.5%) and borotrifluoride diethyl etherate (BD distilled at reduced pressure from over calcium hydride) 3 g dissolved in 100 ml hexane was refluxed during 3 hrs. The hexane was driven out by evaporation, the product was dissolved in ether and washed several times with water. After evaporating the ether, 40 g of a viscous, light yellow product were obtained. The product has the formula

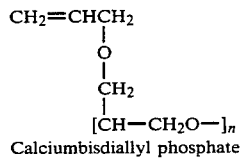

I

Diallylester of phosphoric acid (4 g) was solved in 50 ml water and calcium carbonate in excess was added. On completed reaction followed filtering, and the filtrate was evaporated down in a circulation evaporator. The product was crystallized twice from aqueous ethanol. The yield was 2.3 g of acicular crystals. The product has the formula

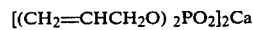

II

MANUFACTURING THE ELECTRODE

Electrode base material

For the electrode base, glass was used which had been made electrically conductive on one side with a thin stannic dioxide course (Libbey-Owens-Ford Company, Glass Division, OH, U.S.A.). The glass plate had size about 20×50 mm. The stannic dioxide was removed on three margins over a few millimeters, using photolithography and electrolytic etching. Electrical contact was established on the unetched edge with mechanical pressure.

Manufacturing the membrane

In 100 ml of ethanol/methanol mixture (5:1) were dissolved 2.0 g telomer (Compound I) and 60 g calciumbisdiallyl phosphate (Compound II). The electrode base plate was coated by spin coating technique: on the spinning plate were applied three consecutive doses of 1 ml each of the solution, drying the plate in an oven between applications. The plate was finally kept for 60 hrs in an oven at 100° C.

Equilibration

The electrode was quilibrated by keeping it 3 days in a solution of molarity $10^{-3}$M with regard to calcium.

MEASUREMENTS

Apparatus

The measurements were carried out in a thermostated (25.0° C.) 50 ml measuring cell (Metrohm). The reference electrode was a silver/silver chloride electrode, connected by a 0.1M NaCl salt bridge to the cell. The potential was measured using a preamplifier (AD515L, Analog Devices) with input resistance $> 10^{13}$ ohms connected to a 4½ digit digital voltmeter.

Results of measurement

The electrode's response to the calcium ion and its selectivity with regard to the sodium ion was determined by measuring the cell potential as a function of calcium concentration in pure water and in a 0.1M aqueous sodium chloride solution. The following table gives as an example the results obtained in one series of measurements.

| $c_{Ca}$, M | Cell potential, mV | |
| --- | --- | --- |
| | In water | In 0.1 M NaCl solution |
| $10^{-6}$ | 57.2 | 103.0 |
| $10^{-5}$ | 70.1 | 107.1 |
| $10^{-4}$ | 94.8 | 114.5 |
| $10^{-3}$ | 123.0 | 130.1 |
| $10^{-2}$ | 150.3 | 157.5 |
| $10^{-1}$ | 176.5 | 195.6 |

The attached drawing shows the cell potentials plotted over the logarithm of calcium ion concentration. It is possible from the graph measured in pure water to estimate for this electrode the calcium ion determination limit: about $10^{-6}$ mol/dm$^3$. The graph derived from measurements in sodium chloride solution gives the selectivity factor $k_{Ca,Na} = 3 \times 10^{-2}$. Thus the selectivity of the electrode is adequate for clinical analyses, for instance.

It is obvious to a person skilled in the art that different embodiments of the invention are not confined to the example presented above and that they may vary within the scope of the attached claims. For instance, it is possible to manufacture in addition to the calcium-selective electrode also electrodes which are selective to other ions, such as e.g. Mg, K, Na, etc. This is simply brought about by using in the manufacturing of the membrane as "template" the desired ion instead of calcium. It is further possible in the manufacturing of the membrane to use, instead of the polymerizable compounds here presented, other polymerizable compounds, the only essential consideration being in that connection that the polymer that is produced is polar enough and has sufficient mechanical strength. It is then possible in the polymerizing step to use other methods as well, on the side of heating, such as plasma polymerizing or UV polymerisation. It is not indispensable either that the electrode is without internal solution: the conventional electrode design may equally be contemplated which carries an internal reference solution between the membrane and the conductive metallic body.

I claim:

1. An ion-selective electrode comprising a body wherein said body is formed from a member selected from the group of conductors and semiconductors and a membrane separating the body from a solution to be measured, said membrane consisting essentially of a crosslinked polymer material prepared by
   (a) polymerizing a mixture comprised of allyloxy-substituted propylene glycol telomer and calcium bisdiallyl phosphate;
   (b) removing ions from the polymerized material by equilibration with a solution of $10^{-3}$ molarity with respect to the ions to be removed said ions of the type to be selected by said electrode, to leave gaps conforming to said ions to be selected.

2. A procedure for manufacturing an ion-selective electrode, said procedure comprising forming a membrane on a body formed from a member of the group of conductors and semiconductors to separate the body from a solution to be measured by
   (a) polymerizing a mixture comprised of allyloxy-substituted propylene glycol telomer and calcium bisdiallyl phosphate with the aid of heat or ultraviolet light;
   (b) removing ions of the type to be selected by said electrode from the polymerized material by equilibration with a solution of $10^{-3}$ molarity with regard to the ions to be removed.

* * * * *